(12) United States Patent
Hill et al.

(10) Patent No.: US 8,361,511 B2
(45) Date of Patent: Jan. 29, 2013

(54) TASTELESS NUTRITIONAL SUPPLEMENT CONTAINING FREE AMINO ACIDS

(75) Inventors: Joanna Hill, Liverpool (GB); Catherine Louise Patterson, Liverpool (GB); Andrew Sean Lynch, Liverpool (GB)

(73) Assignee: SHS International Ltd., Liverpool (GB)

( * ) Notice: Subject to any disclaimer, the term of this patent is extended or adjusted under 35 U.S.C. 154(b) by 336 days.

(21) Appl. No.: 12/440,339

(22) PCT Filed: Sep. 7, 2007

(86) PCT No.: PCT/EP2007/059383
§ 371 (c)(1),
(2), (4) Date: May 19, 2009

(87) PCT Pub. No.: WO2008/028951
PCT Pub. Date: Mar. 13, 2008

(65) Prior Publication Data
US 2010/0009006 A1    Jan. 14, 2010

(30) Foreign Application Priority Data
Sep. 8, 2006 (EP) ...................... 06120377

(51) Int. Cl.
*A61K 9/14* (2006.01)
*A61P 27/14* (2006.01)
(52) U.S. Cl. ........................................ 424/498
(58) Field of Classification Search .................. None
See application file for complete search history.

(56) References Cited

U.S. PATENT DOCUMENTS

| | | | |
|---|---|---|---|
| 5,776,490 A | * | 7/1998 | Chu et al. ............. 424/451 |
| 6,506,422 B1 | * | 1/2003 | Masson et al. ............ 426/2 |
| 2003/0148013 A1 | * | 8/2003 | Jobe et al. ............. 426/635 |

FOREIGN PATENT DOCUMENTS

| | | |
|---|---|---|
| EP | 0 363 879 | 4/1990 |
| EP | 0 388 237 | 9/1990 |
| JP | 58-216118 | 12/1983 |
| JP | 2-042967 | 2/1990 |

OTHER PUBLICATIONS

International Search Report dated Oct. 23, 2007, from corresponding PCT application.

* cited by examiner

*Primary Examiner* — Scott Long
*Assistant Examiner* — Sarah Alawadi
(74) *Attorney, Agent, or Firm* — Young & Thompson

(57) ABSTRACT

A nutritional composition includes proteinaceous material and micronutrients, wherein at least 90 wt % of the proteinaceous material and micronutrients is coated with a fat-containing layer containing at least 90 wt % of edible fat, based on the total weight of the layer, and having a SFC of more than 95% at 30° C., wherein the proteinaceous material includes at least 90 wt % free amino acids, based on its proteinaceous weight content, the micronutrients and proteinaceous material in the coated particulate material forming separate particles, and wherein the coated particulate material and the coating are free from phospholipids. It is preferred that the coating is made from hydrogenated palm oil.

20 Claims, No Drawings

TASTELESS NUTRITIONAL SUPPLEMENT CONTAINING FREE AMINO ACIDS

FIELD OF THE INVENTION

The invention pertains to particulate proteinaceous material-containing nutritional supplement having an improved shelf life, meets specific nutritional requirements, is organoleptically neutral and at the same time acceptable as to processability.

BACKGROUND OF THE INVENTION

Protein nutrition sometimes needs to be adapted to specific metabolic and physiologic conditions, e.g. because persons suffering from an allergy cannot accept certain proteins, or persons suffering from a disorder in amino acid metabolism need supplementation with specific amino acids or need to avoid specific amino acids. For example, Phenylketonuria (PKU) patients often need a lifelong feeding which is low in phenylalanine, and patients suffering from cow's milk allergy are often fed amino acid-based formulas to manage gastrointestinal problems due to food protein allergy.

In those cases, protein nutrition is adapted by providing blends of amino acids or peptides. Such blends may also contain or be combined with other food components such as vitamins, minerals, carbohydrates or lipids. Typically, such products have a powder-like form, which can be reconstituted to a drink or allows admixture with drinks.

However, such powder-like forms cause several problems. Many amino acids are poorly palatable because of bad taste. For example the branched chain amino acids leucine, isoleucine, valine, threonine, the acid amino acids glutamic acid and aspartic acid, tyrosine, phenylalanine, histidine, tryptophan and cysteine are poorly soluble, have bad organoleptic properties or may interact with other components in the mixture-giving rise to poor taste and appearance. Also, particles of such amino acids in dry form may have different sizes, which may cause inhomogeneities in the final product due to a varying degree of settlement during storage. Very small particles, may cause a dust when the package is opened or the powder is transferred.

Numerous ways of manufacturing dry or semi-dry products that comprise a large amount of free amino acids have been suggested. In most cases the synthetic ingredients are obtained in dry form which are either blended in dry form or dissolved in an aqueous phase, optionally together with other ingredients, optionally blended with a lipid phase, homogenised, heat-treated and evaporated and spray-dried to produce a powder which could also be agglomerated. Such agglomerates consist of powder particles, which comprise all ingredients which have been spray-dried and which typically include digestible carbohydrates, vitamins a lipid phase and minerals.

For example, to obtain a stable amino acid preparation not having a smell, a taste and an unpleasant texture after taking, not causing any side effect, JP 58216118 teaches the mixing of an amino acid with 10-30 wt % of higher fatty acids, waxes, carbowaxes, triglycerides (e.g. stearic acid, bees wax, polyethylene glycol 4000, Witepsol), which are solid at normal temperature and are pharmacologically permissible. After melting and homogenising, the mixture is solidified. However, it requires large amounts of these fatty acids to end up with an acceptable taste improvement, thus disadvantageously increasing the dosage in situations where the uptake is often already causing problems. Consumption of large amounts of fatty acids and waxes may also be undesired for health reasons. The products, or their spray-dried counterparts, develop Maillard products during production or storage, and interactions may occur between reactive amino acids and vitamins.

Although U.S. Pat. No. 6,506,422 mentions the use of encapsulated amino acids for administration to phenylketonuria patients, in fact it discloses ground mixtures of amino acids and fats with the aforementioned problems. Example 4, concerning encapsulated amino acids, only describes simple mixing of amino acids and fat mix at 70° C., homogenization and cooling to 30° C. However, such a process would not yield satisfactory shielding of the bad-tasting amino acids. Further, the so called encapsulation in U.S. Pat. No. 6,506,422 only involves a limited amount of amino acids, i.e. lysine, methionine, tryptophan and valine. The cooled fat-treated mixture is added to another amino acid mixture. Hence, the formula thus prepared may be suitable for admixture with drinks, it would exude an odour and/or taste which would be noticeable in every meal due to the fact that many components will interact on reconstitution as they are not coated, giving an unpleasant taste. Even if pleasant, its dominant taste and odour will eventually annoy a patient sentenced to lifelong administration of such nutritional formula, especially since he or she must take considerable quantities of the phenylalanine-free mixture of amino acids with his or her meals.

Moreover, U.S. Pat. No. 6,506,422 states that lecithins may be present in the composition, for establishing stability during reconstitution in hot water. The lecithin does not contribute to the stability of the encapsulated product. With lecithin high amounts of polyunsaturated fatty acids are introduced, which will easily oxidise during shelf life, thus disadvantageously resulting in off-flavours and potential toxic reaction products.

JP 2042967 provides a non-lipophilic substance, for instance an amino acid or crude drug, with a coating by attaching a surfactant and a phospholipid to the surface of the substance, and applying oil and fat exhibiting crystalline state at normal temperature (e.g. palm oil or beef tallow) to the surface. The surface of the substance coated with the oil and fat film is then coated with a phospholipid (e.g. lecithin) dissolved in a solvent (e.g. ethanol), and the solvent is removed to easily perform the coating of the substance and mask the disagreeable taste and odour of the substance. Again, the resulting coated substance disadvantageously involves multiple layers with phospholipids, especially lecithin.

EP-A-363.879 uses a gelling agent for encapsulation of amino acids and mentions that hard fat may be used for encapsulation to mask the taste and to prolong the life of the amino acids in the stored product. It is clear from the examples that a vitamin-mineral premix is coated together with the amino acids. Apparently, the solution given there is not considered satisfactory, since the composition further contains dried or candied fruit. It is the inventors' findings that this may well be caused by interactions between amino acids and other active ingredients, such as the micronutrients.

US-A-2003/148013 discloses the use of zinc stearate as a coating material for amino acids and micro nutrients. This product solves the problem of leaching. Also here, lecithin is one of the mentioned fats for use in the coating material.

EP-A-388.237 describes compositions comprising lecithin as an emulsifier, thereby denying the problem of deterioration of the coating. Furthermore, nothing is done to prevent contact between micronutrients and amino acids either.

Hence, there is a need for a dry or semi-dry free amino acid-containing nutritional supplement having a homogeneous particle size distribution, which product has a neutral taste and comprises low amounts of off-flavours and deterioration of active components, allowing acceptable admixture with foodstuffs.

DESCRIPTION OF THE INVENTION

It is an object of the invention to provide a free amino acid-containing nutritional supplement having neutral taste and odour, mouthfeel and texture, good homogeneity characteristics, and an improved shelf life.

It is also an object of the present invention is to create a dietetic supplement which shall be more readily acceptable to patients suffering from metabolic diseases or GI allergy, for instance PKU patients. It is especially intended for patients suffering from metabolic diseases related to protein malfunction or disorders in amino acid metabolism. The dietetic supplement may be protein-free or allergen-free, or may contain hypoallergenic proteins, for addition to non-allergenic foods.

It is found that these objects can be achieved by fat coating and optionally micronizing the taste-contributing ingredients in a dietetic supplement, especially the bad-tasting ingredients therein. A suitable fat-containing layer should contain at least 90 wt % of edible fats and oils and have a Solid Fat Content (SFC) of more than 70% at 37° C. The high SFC guarantees that the layer will not melt upon chewing, thus loosing its effect of masking the bad taste of the supplement. The invention thus pertains to a nutritional supplement consisting of proteinaceous material and micronutrients, wherein at least 90 wt % of the proteinaceous material and micronutrients is coated with a fat-containing layer containing at least 90 wt % of edible fat, based on the total weight of the layer, and having a SFC of more than 70% at 37 C., preferably more than 95% at 30° C., and wherein the proteinaceous material comprises at least 90 wt % free amino acids, based on its proteinaceous weight content. Preferably at least all proteinaceous material is coated. The micronutrients may further be micronized. Preferably, the uncoated remainder of the supplement may be formed from micronutrients, provided that these micronutrients do not contribute to the organleptic properties of the supplement. The supplement is preferably characterized as tasteless and odourless.

However, in a preferred embodiment, the invention pertains to a nutritional composition consisting of particulate material of proteinaceous material and micronutrients, wherein at least 90 wt % of said proteinaceous material and micronutrients is coated with a fat-containing layer containing
   a. at least 90 wt % of edible fat, based on the total weight of the layer, and
   b. having a Solid Fat Content (SFC) of more than 70% at 37° C., and
wherein said proteinaceous material comprises at least 90 wt % free amino acids, based on its proteinaceous weight content,
said micronutrients and proteinaceous material in the coated particulate material forming separate particles,
and wherein said coated particulate material and the coating are free from phospholipids.

Advantageously, the nutritional supplement may be admixed with any food or drink without contributing, either pleasantly or negatively, to the odour and or taste thereof. Hence, the invention allows a patient in need thereof to incorporate protein substitutes and micronutrients in existing foods, such as crisps, mashed potatoes. Alternatively, the nutritional supplement may be an integrated part of a new food form, such as a bar containing the proteinaceous material and micronutrients.

The ability to incorporate the supplement in food or new product lines is considered desirable especially in those cases where a patient is to consume protein substitutes for longer time periods, for instance PKU patients.

The nutritional supplement is suitable for patients suffering from protein-related metabolic diseases, malfunctioning amino acid metabolism or food allergies.

Nutritional Supplement

The nutritional supplement is preferably a homogenized powder. Its moisture content is preferably less than about 5% by weight. Such a powder could be obtained from a homogenized liquid mixture by transferring it to a suitable drying apparatus such as a spray drier or freeze drier and converted to powder. Any heat-sensitive components may be added to the powder at this point.

In a preferred embodiment the formula is prepared by mixing together, in powdered form, the proteinaceous material, vitamins, and minerals after being coated. It is of course possible to place all the ingredients into liquid form as described above and then spray dry them to powder, but this is not necessary.

The micronutrients and proteinaceous material present in the coated particulate material preferably form separate particles, not mixed together in individual particles. This is related to the preparation of the formula, where different needs for coating of these materials exist. It brings the further advantage that interactions between micronutrients and amino acids are thus avoided.

It is preferred that more than 95%, most preferably more than 98% of the dry weight of the supplement is coated.

Since the nutritional supplement is intended as a protein substitute, there are no carbohydrates present in the supplement. However, it may be useful to incorporate a small amount of carbohydrates in the fat-coating layer. There, the amount of carbohydrates is preferably less than 5 wt %. It may provide texture to the coating layer. However, it is preferred that the fat-coating layer is free from carbohydrates, in order to reduce the risk of Maillard reaction and support shelf life of the product.

The amount of the nutritional formula required to be fed to a patient will vary depending upon factors such as the patient's condition, the patient's body weight, the age of the patient, and whether the nutritional formula is the sole source of nutrition. However the required amount may be readily set by a medical practitioner. In general, sufficient of the nutritional formula is administered to provide the patient with about 1 g protein to about 4.0 g protein per kg of body weight per day. If the nutritional formula is used as a supplement to other foods, the amount of the nutritional formula that is administered daily may be decreased accordingly.

It is observed that best mouthfeel and taste characteristics are obtained with coated particulate material having a size between 60 and 3,000 μm, and wherein at least 70% is between 60 and 1,000 μm, preferably at least 95% in the range of 125-1,000 μm, and/or preferably at least 95% between 150 and 1,500 μm.

For measuring the size of the particulate material a sieve test is performed according to the manufacturers operating instructions for the model AS200 analytical sieve shaker. The manufacturer is Retsch GmbH & Co. KG , 42781 Haan, Rheinische Str.36, Germany.

The invention further pertains to a food item containing the nutritional composition. The composition may be present in or on the food item. It may be used as a protein substitute in solid or semi-solid foods, for instance sprinkled on crisps, mashed in potato etc. Alternatively, new food items may be prepared by incorporating the nutritional supplement therein.

Since the nutritional supplement provided by the invention is neutral in terms of taste and smell, its incorporation in foods does not require additional flavourings for compensation.

Particulate Proteinaceous Material

The proteinaceous material preferably provides at least about 30% of the energy, preferably 40-60 en % of the powdered nutritional supplement. In terms of weight, it is preferred that the proteinaceous material forms 40-95 wt %, preferably 50-80 wt % of the dry weight of the supplement.

"Proteinaceous" material is understood to comprise mainly free amino acids. It may further include di- or tripeptides, and a non-allergenic protein source in those cases where the supplement is to be consumed by patients suffering from GI allergy. However, it is preferred that the proteinaceous material contains at least 95 wt % amino acids.

In the most preferred embodiment the proteinaceous material consists of free amino acids. The amino acids present in the dietetic supplement of the invention may be present in any suitable form, especially in any form appropriate for foodstuffs. Illustratively the amino acids may be present as equivalents, e.g. in the form of salts, hydrochlorides, hydrates, acetates and maleates etc. Again the amino acids may be used in the form of dipeptides as long as these dipeptides do not contain contra-indicated amino acids, such as phenylalanine in PKU.

Although especially methionine, cysteine, lysine and tryptophan are generally appreciated as the bad-tasting amino acids, it is the findings of the invention that for a neutral or flavour-free taste all proteinaceous material should be covered by the fat coating. It prevents any of the free amino acids, even the sweet-tasting ones such as proline and serine, to contribute or even dominate the taste and/or smell of a food to which the nutritional supplement containing the free amino acids is added. This allows for an increase variety of food types to which the coated material may be added.

In order to provide a nutritional supplement which would ensure the required daily intake of protein and amino acids, it should at least contain all essential amino acids.

For infants under the age of 2 years, Arg, Cys, Gln, His, Ile, Leu, Lys, Met, Thr, Trp, Tyr, Phe and Val are considered to be essential or conditionally essential amino acids which should be included. For children over the age of 2 years or adults, the list of essential or conditionally essential amino acids present in the supplement consists of Cys, His, Ile, Leu, Lys, Met, Thr, Trp, Tyr, Phe and Val. These essential amino acids preferably form 50-90 wt %, more preferably 60-80 wt % of all proteinaceous material present in the supplement. The supplement may further contain one or more of the non-essential amino acids Gly, Ala, Asp, Pro, Ser, preferably in a total amount of 10-50 wt %, more preferably 20-40 wt %, based on all proteinaceous material in the supplement.

Organoleptically poor amino acids Met, Cys, Lys and Trp, or equivalents thereof, are present in the proteinaceous material in an amount of 7.5-22 wt %.

Amino acids Pro and Ser, generally appreciated as sweet-tasting amino acids, contribute in an amount of 7-15 wt % to the proteinaceous material.

In a preferred embodiment the proteinaceous fraction of the nutritional supplement preferably comprises 4-8% Gly, 1-5% Ala, 4-8% Arg, 4-8% Asp, 0.5-4% Cys, 9-13% Glu, 1-5% His, 4-8% Ile, 8-12% Leu, 6-10% Lys, 0.5-4% Met, 5-9% Pro, 2-6% Ser, 2-6% Thr, 0.5-4% Trp, 7-11% Tyr and 4-8% Val, or their respective equivalents, based on the total weight of proteinaceous material.

For its suitability as a diet for PKU patients, the nutritional supplement has a low Phe content, although Phe is characterized as an essential amino acid. The coated proteinaceous material preferably contains less than 0.5 wt % phenylalanine, based on its total proteinaceous content, and is more preferably free from phenylalanine, thus rendering the particulate material suitable for administration to patients suffering from phenylketonuria. The supplement may also provide an excess of Tyr to compensate for the inability of PKU patients to metabolise Phe into Tyr. The nutritional supplement preferably provides an amount of Tyr which is greater than the amount recommended.

Modifications will readily occur to those skilled in the art, especially when the supplement is to be consumed by patients suffering from metabolic disorders or food allergies other than PKU. The supplement will have to be adapted to the particular needs of the patients, based on existing formulations.

Micronutrients

Vitamins, minerals and trace elements are additionally integrated into the nutritional supplement, since a PKU-afflicted patient would not receive these nutrients in adequate amounts from a phenylalanine-low diet. Likewise, patients suffering from other metabolic diseases or food allergies may have similar problems to consume these micronutrients in amounts sufficient to meet their daily requirements. Therefore, these micronutrients are also incorporated in the supplement.

If vitamins are included in the supplement, these are also subjected to coating, although the reason for doing so may be different. The shelf life of these vitamins may be extended by coating them with a fat layer. Suitable examples of coated vitamins for incorporation in the supplement are vitamin A, B, in particular B1, B2 and B6, D, in particular D3, E and K.

These vitamins may be provided with a coating individually, thus forming separate fat-coated powders. Alternatively, one or more vitamins may first be mixed together, and only then subjected to coating. Therein, it is preferred to use the same coating as the proteinaceous material is provided with. However, it is important to realize that the coating materials also contribute to the energy and volume content of the supplement. Hence, if coating is not necessary in terms of taste or shelf life improvements of a particular ingredient, it may be left uncoated. Furthermore, for coating heat-labile micronutrients, it may be favourable to use fats having a relatively low temperature.

Where necessary, the powdered micronutrients may be subjected to a micronizing or milling treatment, of which is known in the art to reduce the organoleptic perception of the powder. It may further be of help in providing a substantially homogenous particle distribution. However, the invention relies primarily on fat encapsulation for solving the problem of bad organoleptic taste, micronization may only be of assistance therein.

Coating

The SFC of the fat coating is more preferably at least 90% at 37° C. If the supplement is intended for use in or hot foods, it is preferred to use coatings having an even higher SFC, to prevent the coating from melting before and during consumption. Preferably the SFC is at least 95% at 37° C. The SFC is measured as the amount of solid fat relative to the total amount of fat of the coating, in accordance with ISO 8292 (NMR pulse).

Although the term "oil" is often used in the art to characterise fats which are in liquid form at room temperature, in the context of the invention the terms "fat" and "oil" are considered interchangeable. Both fats and oils may be applied, provided that the melting behaviour of the fat coating fulfils the SFC requirement of the invention. Obviously, for incorporation in a nutritional supplement or food composition, the fats and oils applied should be edible.

The fat should be selected such that the coating layer has a very good resistance to melting during storage, distribution, but also during chewing. Especially the latter requirement puts high demands on the fat coating properties, as bad taste release of the coated amino acid preparation in the mouth is to be avoided at all cost. In addition, the amount of lower-melting fats should be low to avoid stickiness, and to keep the free-flowing properties of the powder intact. However, it may be required to include some fats which are liquid at a temperature of 20° C., to provide essential fatty acids to the composition. If present, the amount of such liquid fats is preferably less than 5%, most preferably less than 1 wt %. In the most preferred embodiment there are no liquid fats present in the fat-coating layer.

In addition to the required presence of large amounts of fats which are solid at consumption, it is preferred that the fat coating melts at a temperature lower than 70° C., more preferably lower than 60° C. It enables coating of the amino acid preparation to be performed at relatively low temperatures.

The fat-containing coating preferably contains more than 95 wt % fat, more preferably at least 98 wt % fat. More particularly, the coating consists of fat.

Although the invention is not limited in the type of edible fat that can be applied for the preparation of the fat coating. It may require hydrogenation to increase its melting point in the desired range. Although the invention is not limited in the type of fat that can be applied for the preparation of the fat coating, it is preferred to use fats selected from the group consisting of cocoa butter, illipe, shea, palm, sal, soybean, cottonseed, palm kernel, coconut, rapeseed and sunflower oil, where necessary in hydrogenated form, or fractions or blends thereof.

The most suitable candidates for incorporation in the fat coating are (hydrogenated) palm oil and hydrogenated soybean oil. It is preferred that at least 90%, more preferably at least 95% of the fat fraction of the fat-containing coating is (hydrogenated) palm oil, a naturally occurring and nutritional oil making the coating less prone to oxidation. Hydrogenated soybean oil may be avoided in case the amino acid preparation is to be administered to patients suffering from gut allergy.

Most preferably, (hydrogenated) palm oil is the only fat source in the coating layer, in particular hydrogenated palm oil. Hydrogenated palm oil has a high melting point, making it safe to use the coated particulate material in or on hot foods.

The fat coating preferably contains less than 5%, most preferably less than 1% unsaturated fatty acids, because triglycerides containing unsaturated fatty acids are known to melt first, while those containing saturated and trans isomers of fatty acids melt at higher temperature. The fat coating may preferably be characterised by a fatty acid profile predominant in C16:0 and C18:0, palmitic and stearic acid, respectively. The fat composition is especially low in polyunsaturated fatty acids, linoleic acid and linolenic acid being the most important examples thereof, e.g. less than 1 wt %, preferably less than 0.5%, based on the total weight of the fatty acids in the fat coating.

Phospholipids are preferably present in amounts of 0-0.5 wt %, based on the total weight of the fat coating, because these introduce highly unsaturated fatty acids into the coating which are susceptible of initiating oxidation and causing accelerated deterioration of the coating. If phospholipids are applied, these are present in the fat coating layer, not forming any additional layers. In a preferred embodiment the coated particulate material and the coating are free from phospholipids.

The fat coating may include other ingredients such as sweeteners, flavourings, aroma agents, preservatives, colorants, or mixtures thereof. The proportions thereof are determined according to taste and/or appearance. However, in the preferred embodiment the fat coating is free from additives which contribute to taste and smell, as it is desired to provide a neutral-tasting or taste-masked nutritional supplement therefrom.

Fat makes preferably up for 5-50 wt %, preferably 20-40 wt %, more preferably 25-35 wt % of the dry weight of the supplement. Therein, it is preferred that all fat is present in the coating layer of the powder. It is important to choose the amount of fat not too low, in order to guarantee a sufficiently thick masking layer. Secondly, it is preferred not to use large amounts of fat, as it imparts calories and volume to the supplement.

The first step of encapsulation is to melt the fat since, as described above, it is a hard dry fat at room temperature. The ingredients to be encapsulated may be introduced into a fluidized bed reactor. The air flow passing through the reactor is adjusted so that the particles are slightly levitated. The liquidized and free flowing fat is then sprayed over the ingredients in the fluidized bed reactor, thereby encapsulating it. The fluidized air levitating the ingredient is cooled, thereby causing the fat to solidify and encapsulate the ingredient. After the desired amount of coating is applied, the encapsulated ingredient is then removed from the fluidized bed reactor and optionally sifted for size. While the use of a fluidized bed reactor is herein described for the encapsulation process, those skilled in the art will realize that other encapsulation processes such as spray drying, spray chilling, spinning disk and coacervation may be used. Details on encapsulation may for instance be found in U.S. Pat. No. 6,153,236.

In an alternative embodiment, the invention pertains to a nutritional composition consisting of proteinaceous material comprising at least 90 wt % free amino acids based on its proteinaceous weight content,
 a. wherein at least 90 wt % of said proteinaceous material is coated with a fat-containing layer containing at least 90 wt % of edible fat, based on the total weight of the layer; and
 b. wherein said coated particulate material has a size between 60 and 3,000 μm, with at least 70% thereof between 60 and 1,000 μm.

The nutritional composition according to this embodiment may further contain one of the aforementioned features. Special mention is made of the preferred embodiments in which the particulate material and its coating are low in phospholipids, preferably free from phospholipids, for the aforestated reasons, and/or wherein the fat-containing layer has a Solid Fat Content of more than 95% at 37° C., more preferably more than 90% at 30 C. The composition may further contain micronutrients.

EXAMPLE

Example 1

Fat-coated Amino Acid Composition

A tasteless powder free from phenylalanine was prepared, having the following balanced amounts of the other essential and non-essential amino acids and fat, having a protein equivalent of 61 g/100 g powder, and a caloric value of about 480 cal/100 g powder.

| Amino Acid Profile (g/100 g Powder) | |
|---|---|
| L-ALANINE | 2.19 g |
| L-ARGININE | 4.14 g |
| L-ASPARTIC ACID | 3.91 g |
| L-CYSTINE | 1.50 g |
| L-GLUTAMIC ACID | 0 g |
| GLYCINE | 3.91 g |
| L-HISTIDINE | 2.30 g |
| L-ISOLEUCINE | 3.68 g |
| L-LEUCINE | 6.21 g |
| L-LYSINE | 4.83 g |
| L-METHIONINE | 1.03 g |
| L-PROLINE | 4.49 g |
| L-PHENYLALANINE | 0 g |
| L-SERINE | 2.88 g |
| L-THREONINE | 2.99 g |
| L-TRYPTOPHAN | 1.27 g |
| L-TYROSINE | 5.52 g |
| L-VALINE | 4.03 g |
| L-ASPARAGINE | 0 g |
| L-CITRULLINE | 0 g |
| L-CARNITINE | 0 g |
| TAURINE | 0 g |
| L-GLUTAMINE | 6670 g |
| TOTAL AMINO ACIDS | 61.53 g |

The powder was coated with hydrogenated palm oil, solid at room temperature. The melting point of the coating was about 57° C. The amount of fat was 30 g per 100 g powder. The fatty acid profile was characterised as:

| Fatty Acid Profile (g/100 g Fatty Acids) | |
|---|---|
| C12:0 | 0.2 |
| C14:0 | 0.9 |
| C15:0 | 0.1 |
| C16:0 | 39.5 |
| C17:0 | 0.1 |
| C18:0 | 56.5 |
| C18:1 | 1.6 |
| C20:0 | 0.5 |
| C22:0 | 0.1 |
| C23:0 | 0.4 |
| C24 | 0.1 |

Example 2

Amino Acid Profile (g/100 g Powder)

Similar to example 1, a tasteless powder free from phenylalanine was prepared, having the following balanced amounts of the other essential and non-essential amino acids and fat, having a protein equivalent of 59 g/100 g powder, and a caloric value of about 480 cal/100 g powder.

| L-Alanine | 2.4 |
|---|---|
| L-Arginine | 4.5 |
| L-Aspartic Acid | 4.2 |
| L-Cystine | 1.7 |
| L-Glutamic Acid | nil added |
| Glycine | 4.2 |
| L-Histidine | 2.5 |
| L-Isoleucine | 3.9 |
| L-Leucine | 6.7 |
| L-Lysine | 5.2 |
| L-Methionine | 1.1 |
| L-Phenylalanine | nil added |
| L-Proline | 4.8 |
| L-Serine | 2.9 |
| L-Threonine | 3.2 |
| L-Tryptophan | 1.3 |
| L-Tyrosine | 5.9 |
| L-Valine | 4.3 |
| L-Glutamine | 7.3 |
| L-Carnitine mg | nil added |

The amino acid preparation was coated as described for example 1.

Example 3

A tasteless powder was prepared from coated micronutrients and amino acids:
Composition of Premix per 100 G:
Thiamine (as Thiamin Mononitrate) 1.2 mg*
Vitamin A (as Acetate) 2690.64 IU*
Vitamin D3 (as Cholecalciferol) 408 IU*
Vitamin E (as acetate) 13.6 IU*
Biotin 0.151 mg
Folic Acid (USP-FCC) 0.706 mg
Niacin (as Niacinamide, USP-FCC) 20.3 mg*
Pantothenic Acid (as D-Calcium Pantothenate, USP) 5.1 mg
Vitamin B12 (as Cyanocobalamin, USP) 5.1 mcg
Vitamin B2 (as Riboflavin, USP-FCC) 1.4 mg*
Vitamin B6 (as Pyridoxine HCl) 1.6 mg*
Vitamin C (as Ascorbic Acid) 50 mg*
Vitamin K1 (as Phytonadione) 71 mcg*
Calcium (as Tricalcium Phosphate, FCC) 1011 mg & (Gluconal-A, FCC)
Chromium (as Chromium Chloride (6H2O)) 29.9 mcg
Copper (as Copper Gluconate) 1.5 mg*
Iodine (as Potassium Iodide, USP-FCC) 0.204 mg
Iron (as Ferrous Sulfate) 15.3 mg*
Magnesium (as Magnesium Phosphate, FCC) 305 mg
Manganese (as Manganese Sulfate, USP-FCC) 1.7 mg
Molybdenum (as Sodium Molybdate) 70.6 mcg
Phosphorous (as Magnesium Phosphate, FCC) 780 mg & (Tricalcium Phosphate, FCC)
Selenium (as Sodium Selenite) 75.7 mcg
Zinc (as Zinc Sulfate, USP-FCC) 11.3 mg
Choline (as Choline Bitartrate) 429 mg*
Meso-Inositol (FCC) 115 mg
Composition of Coated Amino Acid per 92 g:
Glycine (USP) 3.7 g
L-Alanine (USP-FCC) 2.1 g
L-Arginine (as 1-arginine 1-aspartate) 4.0 g
L-Aspartic Acid (FCC) 3.7 g & (1-arginine 1-aspartate)
L-Cystine (FCC) 1.5 g
L-Glutamine (FCC) 6.5 g
L-Histidine (USP-FCC) 2.3 g
L-Isoleucine 3.6 g
L-Leucine 6.0 g
L-Lysine (as L-Lysine Acetate, USP) 4.6 g
L-Methionine (N-acetyl L-Methionine, FCC) 1.0 g
L-Proline (USP-FCC) 4.3 g
L-Serine (USP-FCC) 2.8 g
L-Threonine (USP-FCC) 2.9 g
L-Tryptophan (USP) 1.2 g
L-Tyrosine 5.4 g
L-Valine (USP) 3.9 g

*Coated Material

Both the powdery vitamin premix identified with "*" and the amino acid composition were coated with hydrogenated palm oil, solid at room temperature. The melting point of the coating was about 57° C. The amount of fat was 30 g per 100 g powder. The fatty acid profile characteristics are given in example 1. After encapsulation, the vitamin premix and amino acid composition, including the coated parts, were mixed together.

Example 4

Particle Size Distribution of Coated Material

Particle size distribution of the coated material was measured using the model AS200 analytical sieve shaker.

| Particle Size Range (microns) | Analyte (Wt. g) | Analyte (%) |
| --- | --- | --- |
| Base | 0.07 | 0.14 |
| 45 | 0.38 | 0.73 |
| 63 | 4.51 | 8.71 |
| 125 | 24.13 | 46.58 |
| 250 | 14.97 | 28.90 |
| 500 | 5.29 | 10.21 |
| 710 | 2.07 | 4.00 |
| 1000 | 0.38 | 0.73 |
| >2000 | 0.00 | 0.00 |
| TOTAL | 51.80 | 100.00 |

The invention claimed is:

1. A nutritional composition comprising particulate material of proteinaceous material and micronutrients, wherein at least 90 wt % of said proteinaceous material and micronutrients are coated with a fat-containing layer comprising:
   at least 90 wt % of edible fat, based on the total weight of the layer, and
   a Solid Fat Content (SFC) of more than 70% at 37° C., and wherein,
   the proteinaceous material comprises at least 90 wt % free amino acids, based on total weight of the proteinaceous material, and
   said particulate material of micronutrients and proteinaceous material are each individually and separately coated with the fat-containing layer, forming separate coated particles.

2. The nutritional composition according to claim 1, wherein said coated particles have a size between 60 μm and 3,000 μm, and at least 70% of said coated particles have a size between 60 μm and 1,000 μm.

3. A nutritional supplement for the treatment of patients suffering from food allergies, said supplement comprising the nutritional composition according to claim 1.

4. A nutritional supplement for the treatment of patients suffering from food allergies, said supplement comprising the nutritional composition according to claim 2.

5. The nutritional composition according to claim 1, for the treatment of patients with food allergies.

6. The nutritional composition according to claim 2, for the treatment of patients with food allergies.

7. The nutritional composition according to claim 1, for the treatment of patients suffering from phenylketonuria.

8. The nutritional composition according to claim 2, for the treatment of patients suffering from phenylketonuria.

9. The nutritional composition according to claim 1, wherein the fat-containing layer is free from phospholipids.

10. The nutritional composition according to claim 1, wherein the proteinaceous material comprises dipeptides.

11. The nutritional composition according to claim 1, wherein the proteinaceous material comprises a mixture of at least two free amino acids.

12. The nutritional composition according to claim 1, wherein the proteinaceous material comprises: 4-8 wt % Gly; 1-5 wt % Ala; 4-8 wt % Arg; 4-8 wt % Asp; 0.5-4 wt % Cys; 9-13 wt % Glu; 1-5 wt % His; 4-8 wt% Ile; 8-12 wt% Leu; 6-10 wt% Lys; 0.5-4 wt % Met; 5-9 wt % Pro; 2-6 wt % Ser; 2-6 wt % Thr; 0.5-4 wt % Trp; 7-11 wt % Tyr and 4-8 wt % Val, based on total weight of the proteinaceous material.

13. The nutritional composition according to claim 1, wherein the proteinaceous material comprises Cys, His, Ile, Leu, Lys, Met, Thr, Trp, Tyr, Phe and Val in a combined amount of 60-80 wt %, and Gly, Ala, Asp, Pro and Ser in a combined amount of 20-40 wt %, based on total weight of the proteinaceous material.

14. The nutritional composition according to claim 1, wherein the proteinaceous material comprises Met, Cys, Lys and Trp in a combined amount of 7.5-22 wt %, based on total weight of the proteinaceous material.

15. The nutritional composition according to claim 1, wherein the proteinaceous material comprises Pro and Ser in a combined amount of 7-15 wt %, based on total weight of the proteinaceous material.

16. The nutritional composition according to claim 1, wherein the proteinaceous material comprises less than 0.5 wt % Phe, based on total weight of the proteinaceous material.

17. The nutritional composition according to claim 1, wherein the fat-containing layer comprises less than 5 wt % of carbohydrates.

18. The nutritional composition according to claim 1, wherein the fat-containing layer comprises less than 1 percent unsaturated fatty acids.

19. The nutritional composition according to claim 1, wherein the fat-containing layer comprises more than 50 percent of C16:0 and C18:0 fatty acids.

20. The nutritional composition according to claim 1, comprising 5-50 wt % of fat, based on total weight of the composition.

* * * * *

UNITED STATES PATENT AND TRADEMARK OFFICE
CERTIFICATE OF CORRECTION

PATENT NO. : 8,361,511 B2  Page 1 of 1
APPLICATION NO. : 12/440339
DATED : January 29, 2013
INVENTOR(S) : Hill et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 475 days.

Signed and Sealed this
First Day of September, 2015

Michelle K. Lee
*Director of the United States Patent and Trademark Office*